United States Patent [19]

Sportsman

[11] Patent Number: 5,491,096
[45] Date of Patent: Feb. 13, 1996

[54] ANTIGEN DETECTION WITH AFFINITY CHROMATOGRAPHY AND PARALLEL PROCESSING A CONTROL

[75] Inventor: J. Richard Sportsman, Palo Alto, Calif.

[73] Assignee: Eli Lilly and Company, Indianapolis, Ind.

[21] Appl. No.: 172,843

[22] Filed: Dec. 27, 1993

[51] Int. Cl.$^6$ .................... C01N 33/543; C01N 33/546
[52] U.S. Cl. .................... 436/518; 210/198.2; 210/656; 210/659; 422/59; 422/69; 422/70; 435/287.2; 435/288.6; 436/161; 436/529; 436/530; 436/531; 436/534
[58] Field of Search .................... 422/59, 69, 70; 210/198.2, 656, 659; 530/412, 413; 435/287, 291; 436/161, 518, 529–531, 534

[56] References Cited

U.S. PATENT DOCUMENTS

| | | | |
|---|---|---|---|
| 3,458,437 | 7/1969 | Ovans | 210/31 |
| 3,846,074 | 3/1972 | Tulumello et al. | 422/70 |
| 3,923,460 | 12/1975 | Parrott et al. | 436/161 |
| 3,981,179 | 9/1976 | Roof | 210/198 |
| 4,016,074 | 4/1977 | Porter | 210/198 |
| 4,137,161 | 1/1979 | Shimada et al. | 210/659 |
| 4,551,429 | 11/1985 | Freytag et al. | 435/14 |
| 4,879,247 | 11/1989 | Ohlson | 436/527 |
| 4,895,809 | 1/1990 | Schlabach et al. | 436/541 |
| 4,937,200 | 6/1990 | Kumazawa et al. | 436/541 |
| 4,988,447 | 1/1991 | Hellinger | 210/659 |
| 4,990,250 | 2/1991 | Hellinger | 422/70 |
| 5,234,586 | 8/1993 | Afeyan et al. | 422/70 |

FOREIGN PATENT DOCUMENTS 0200381  5/1986  European Pat. Off.

OTHER PUBLICATIONS

Journal of Chromatograph, 175 (1979) 269–281 Elsevier Scientific Publishing Company, Amsterdam, J. A. Fulton et al. "Dual–Detector–Post–Column Reactor System for the Detection of Isoenzymes Separated by High–Performance Liquid Chromatography".

*Primary Examiner*—David Saunders
*Assistant Examiner*—Christopher L. Chin
*Attorney, Agent, or Firm*—Woodard, Emhardt, Naughton, Moriarty & McNett

[57] ABSTRACT

A method and device for detecting the presence of a suspected antigen in a sample whereby the antigen is trapped using affinity chromatography and the remaining eluant is differentially analyzed against a parallel processed control. The sample is first chromatographically segregated into distinct zones and the resulting eluant is split into two streams. One stream is contacted with a solid phase having immobilized capture ligands specific to the antigen of interest. The other stream is passed through a similar solid phase where the capture ligands have been omitted. The two streams are then differentially analyzed, for example, with ultraviolet light absorption.

12 Claims, 8 Drawing Sheets

5,491,096

ANTIGEN DETECTION WITH AFFINITY CHROMATOGRAPHY AND PARALLEL PROCESSING A CONTROL

BACKGROUND OF THE INVENTION

This invention pertains to a method and a device to assay chromatographic eluate for antigens of interest where affinity chromatography is used in parallel with a control.

An antigen is a chemical or biological substance capable of eliciting production of antibodies when it is introduced into a responding organism. The organism, once challenged by the antigen, responds with the immunological production of structurally complementary antibodies. These antibodies then attack the specific antigen because a particular antibody binds only to those antigens complementary to its structure. Therefore, a particular antibody neglects the other, non-complementary antigens.

Specifically binding pairs of antigens and antibodies are very useful laboratory reagents. Once isolated and purified, particular antibodies may be used to selectively bind to their complementary antigens due to the binding characteristic existing between them. The antibodies are usually tagged with radioactive or fluorescent labels and placed within a reaction vessel. Then, when exposed to a complementary antigen, the antigen-antibody complex forms and tags the presence of the antigen. These complexes may be separated from the reaction vessel and any antigen present is indirectly quantified on the basis of the label present in the complex.

Other uses of specifically binding pairs include competitive binding processes. Similar labels as those mentioned previously are first coupled to antigen molecules. The labelled antigens are then introduced to antibodies in a known amount. Afterward, a chemical or biological sample containing an unlabeled antigen is introduced to the system. The presence and quantity of the unlabeled antigen is then calculated based upon the competition for antibody binding sites using a known amount of labeled antigen to calculate an unknown amount of unlabeled antigen. Such techniques are well known in the art.

Furthermore, it is also known in the art to attach antibodies to a solid support. With attached antibodies, the support becomes a testing material capable of specifically binding labeled or unlabeled antigens. The presence of antigens may then be subsequently detected by monitoring labels as previously mentioned. The attachment of antibodies to a support allows the analytical use of antibodies to be moved from the confines of a reaction vessel to an open system. Particularly, supported antibodies may reside within a continuous flow of effluent, such as, that found in liquid chromatography.

Liquid chromatographic techniques are well known for separating chemical or biological compounds into distinct zones within a suitable eluant. Once separated, analytes may be isolated and further steps may be taken to identify a particular species. However, to avoid the isolation step and to obtain an in-process identification, often an analytical technique such as measuring the eluate's ultraviolet light absorption is used.

In a typical ultraviolet light absorption scheme, a chart recorder or other device continuously records the transmission of ultraviolet light through the flow path of the eluate. When a detectable species enters the detector, the absorption changes from a baseline, the baseline being the absorption seen when only the eluant is present. This change, termed a "peak", marks the passage of a chemical or biological species through the detector. Given that retention time within a chromatographic column is somewhat species specific, the time required for a particular species to flow through the chromatograph should be constant for a particular flow rate of eluant. Therefore, an unknown species may be identified by comparing the retention time of a sample with that of a known and suspected species. However, this method has limitations.

The ultraviolet light absorption scheme directly described above is not applicable in all situations. First, in order to calculate a retention time, an injection or start time must be known. If it is desired to simply monitor a continuous effluent flow; the above scheme would not work because it is not known when a suspected analyte enters the system. A second problem occurs where multiple species have overlapping retention times. It may be particularly difficult to tie a particular species with a particular peak when it may be masked by other chemical species. A third situation occurs when a retention time may slightly change for various reasons. This may result in a false positive or negative when the experimental data is compared to the prior standard.

What is needed is a method and a device that detects "on-line" the presence of a specific antigen without requiring the calculation of retention times, and that is usable in the presence of other chemical or biological species.

SUMMARY OF THE INVENTION

Generally, an affinity chromatography method and device is described for assaying a chromatographic eluate for antigens of interest.

One embodiment of the invention involves a method for determining the presence of a suspected antigen in a sample where the sample is initially segregated into a plurality of distinct zones by chromatography and then split into a first stream and a second stream. The first stream passes through a first solid phase having immobilized capture ligands capable of binding an antigen of interest. The second stream passes through a second solid phase substantially identical to the first solid phase except lacking the immobilized capture ligands. The first and second streams are then analyzed to determine whether the first solid phase differentially absorbed the antigen of interest in contrast with the second solid phase.

Also encompassed by the present invention is a device to determine the presence of an antigen of interest in a sample that includes a means for splitting the flow of eluant from a chromatographic column into a first stream and a second stream. Coupled to the splitting means and accepting the first stream of eluant flow is a capture component with a first solid phase having immobilized capture ligands specific to the antigen of interest. Coupled to the splitting means and accepting the second stream of eluant flow is a control component including a second solid phase substantially identical to the first solid phase except lacking the immobilized capture ligands contained in the capture component. Afterward, one or more detectors reside downstream from each component and are effective to determine a differential absorption of the suspected antigen between the capture component and the control component.

BRIEF DESCRIPTION OF THE DRAWINGS

In the accompanying drawings, forming a park of this specification, and in which like numerals are employed to designate like parts throughout the same.

DESCRIPTION OF THE PREFERRED EMBODIMENTS

Figure 1:
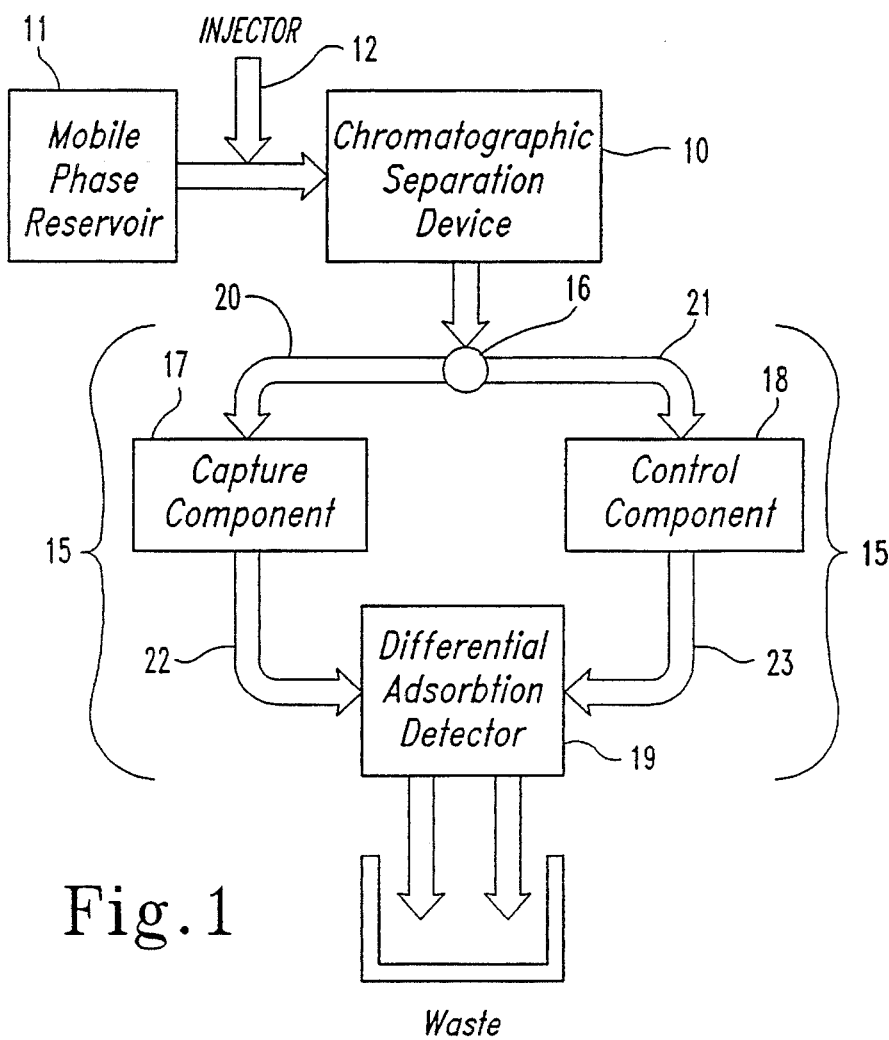
FIG. 1 is a block flow diagram emphasizing the antigen chromatographic separation and post chromatographic detection system of one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 is a block flow diagram emphasizing the antigen chromatographic separation and post chromatographic detection system according to one embodiment of the present invention. A sample containing a plurality of different antigens is introduced into a conventional chromatographic separation device 10. Examples of suitable separation devices include those with a flowing effluent such as liquid chromatographs, high performance liquid chromatographs (HPLC), or electrophoresis devices (capillary zone electrophoresis, elution gel-electrophoresis, etc.). Typically, a mobile phase reservoir of appropriate eluant 11 provides a continuous flow of effluent to elute a sample through the separation device. This may also include a reciprocating pump or a motorized syringe pump for pressurized systems as is necessary to feed eluant through an HPLC.

Continuing with FIG. 1, typically the sample containing the suspect antigen is introduced into the eluant flow for chromatographic separation at 12. The sample enters the chromatographic separation device and exits separated into a plurality of distinct zones. Each zone typically contains similar or isolated chemical species and includes distinct zones of antigens. The distinct zones exiting the separation device and contained in the eluant then pass to the post chromatographic detection system 15.

Post-chromatographic detection system 15 includes a means to split the flow of eluant 16, a capture component 17, a control component 18, and a differential absorption detector 19. The means for splitting the flow of eluant 16 may be as simple as a tubing tee (a pipe fitting) but is preferably a three-way flow splitter valve. Eluant flow exiting chromatographic separation device 10 flows into means for splitting 16 and splits into at least a first stream 20 and a second stream 21. The first stream 20 exits splitter means 16 and then flows into capture component 17. Second stream 21 exits splitting means 16 and then flows into control component 18. It is not critical that streams 20 and 21 have identical flow rates; however, it is preferable that they have reasonably similar flow rates.

Capture component 17 includes a first solid phase with capture ligands immobilized upon the first solid phase. Capture ligands are chemical or biological species that are specific to bind the antigen of interest. Typically, such a capture ligand is the antigen's corresponding antibody; however, other suitable capture ligands include: lectins, recombinant protein A, recombinant protein G, or receptors. The choice of a capture ligand will depend upon the particular suspect antigen because the capture ligand must be capable of binding the antigen of interest within the capture component. Furthermore, a suitable capture ligand must be able to bind to the first solid phase, the stationary substrate contained within the capture component. An example of a suitable solid phase practicable with the present invention includes an HPLC packed column where the packing has recombinant protein A or recombinant protein G attached to the surface. A commercially available example is the POROS® A or G Microcolumn sold by PERSEPTIVE BIOSYSTEMS® of Cambridge, Mass. However, the choice of a stationary substrate compatible with a particular chromatographic effluent and capture ligand, as well as the methods and processes to load capture ligands upon a stationary substrate, are known in the art and are not contemplated by this invention.

Control component 18 is preferably substantially identical to capture component 17. The only critical difference required is that capture component 18 must not contain the capture ligands within it that are contained within capture component 17. Control component 18 serves as a standard for comparison to judge the effects of the capture ligands immobilized within capture component 17. Therefore, it is most preferable that control component 18 be as reasonably identical to capture component 17 as possible except for the omission of the capture ligands. Otherwise, any differential analysis observed between the capture and control components might be attributable to something other than the capture ligands within capture component 17.

Exiting capture component 17 is first stream 22. First stream 22, having passed through the capture ligands immobilized within capture component 17, is depleted of antigens specific to the particular capture ligands. These antigens remain behind in the capture component and are continuously trapped by the capture ligands until all or nearly all of the available binding sites of the capture ligands are saturated. Once saturated, no more antigen-capture ligand complexes can form and excess antigens will resume flow through capture component 17 and out first stream 22. In order to renew effectiveness, the antigen-capture ligand complexes must be broken down and the antigens removed or additional capture ligands must be added to the capture component. Such rejuvenating techniques are well known in the art and are not contemplated by this invention.

Exiting control component 18 is second stream 23. Second stream 23, although passing through a substantially similar component as first stream 22, is not depleted of antigens because control component 18 does not contain immobilized capture ligands specific to retain the antigens of interest. As previously skated, the function of control component 18 is to create a standard for comparison to evaluate the effect of the capture ligands within capture component 17. This standard is second stream 23.

In following, first stream 22 and second stream 23 enter differential absorption detector 19. Differential absorption detector 19 has the function of determining whether the first solid phase contained within capture component 17 has differentially adsorbed an antigen of interest in contrast to the standard exiting the second solid phase. This function may be performed by one or more detectors and in essence requires a method and device(s) capable of evaluating a particular characteristic of streams 22 and 23 that signals when an antigen of interest remains in capture 17 while the same antigen passes through control component 18.

Examples of measurable characteristics that are capable of signalling this difference include ultraviolet light absorption, fluorescence, refractive index, radioactivity, electrochemical activity or any combination of the foregoing. The analytical outputs may then be differentially amplified such that the analytical response of stream 23 is subtracted from the analytical response of stream 22. When the streams are identical, a zero baseline is observed. However, when the streams differ, the difference is signaled by a peak in the differential output. Otherwise, if a differential analysis is not used, a simple contrast in the outputs between the two streams should point to when a particular antigen passes through control component 18 and not capture component 17. After exiting differential absorption detector 19, the eluant flow can then continue to another process or be disposed as waste.

EXAMPLE

Figure 2:
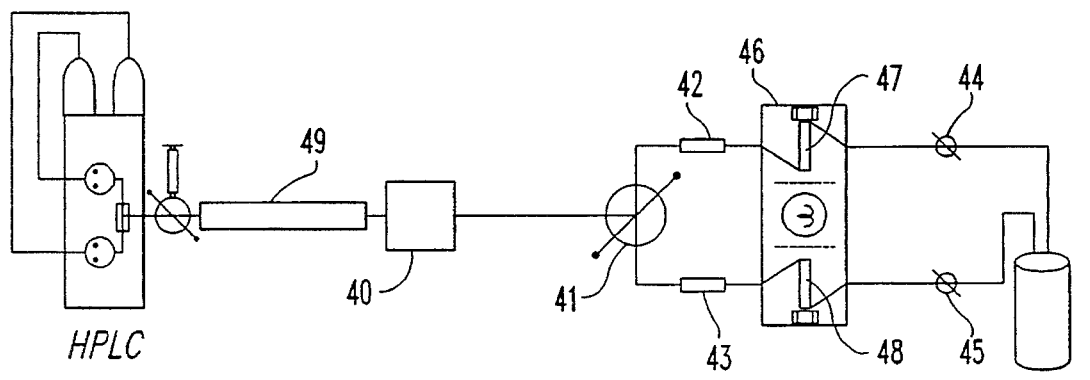
FIG. 2 is a schematic diagram of one embodiment of the present invention.
Figure 3:
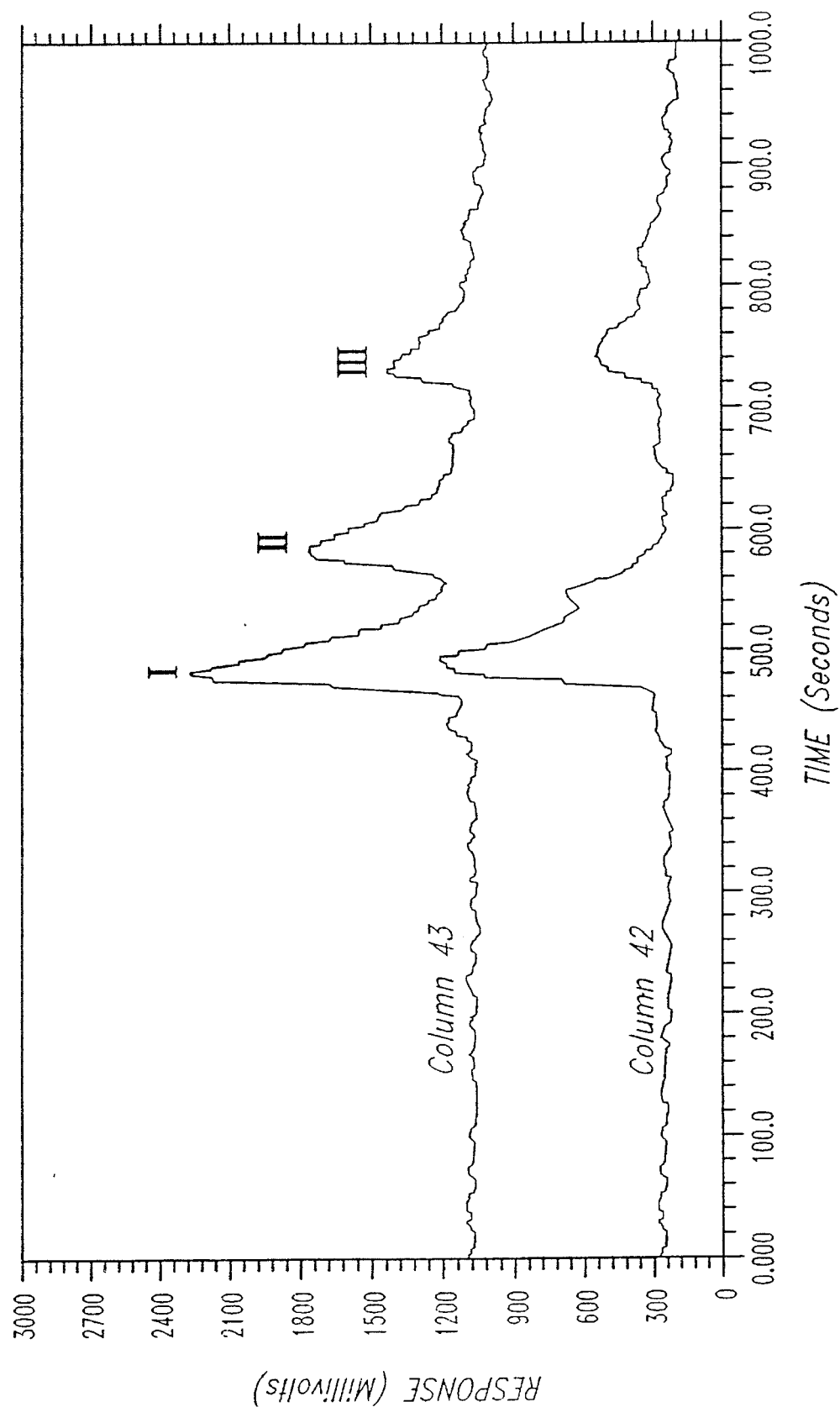
FIGS. 3–9 are liquid chromatography results using ultraviolet detection obtained from one embodiment of the present invention.

Referring to FIG. 2, High Performance Liquid Chromatography (HPLC) column effluent from a SYSTEM GOLD® 167 detector 40 is split equally by three way flow splitter valve 41. The split effluent traverses two miniprotein G affinity columns (42 and 43). The columns 42 and 43 used here are CHROMATO-CHEM® protein A columns; however, identical POROS® G/M columns sold by PERSEPTIVE BIOSYSTEMS® of Cambridge, Mass. are more preferable. Each column is comprised of protein G immobilized on 5 micron silica particles packed into a 2.1 by 20 mm zero dead volume mini-column. Valves 44 and 45 are adjusted to allow matching flow rates. As the split eluant traverses affinity columns 42 and 43, components which bind differentially will be effectively retained for the duration of the run in the column containing the capture antibodies. Hence, these peaks will be missing from the eluant in one of the photometric detector cells of the ISCO® model UA-5 absorbance detector (46) with a type 9 optical unit equipped with matching analytical flow cells 47 and 48 If a specific antibody retains components in column 42 in this manner, relative to a suitable control on column 43, the difference response will be a measure of reactivity of the component with the test antibody in 42.

In the first run, protein G column 42 was loaded with GHC072, an anti-hGH monoclonal mouse antibody from HYBRITECH®. This was accomplished by disconnecting the inlet side of column 42 and injecting with a syringe 1.0 mL of 1.0 mg/mL GH072 in mobile phase (50 mM $Na_2SO_4$, 17 mM tris, pH 7.2). Column 43 was left unloaded. After reconnecting column 42 and washing off unbound antibody, the sample (2.5 mg/mL BSA, 1.0 mg/mL hGH, 0.01 mg/mL cytidine; same throughout all these runs) was chromatographed on ZORBAX® GF-250 (size exclusion) column 49. 20 μL of sample was injected and detectors were set at 0.1 AUFS.

Injections No. 1 and No. 2 offered nearly identical data. FIG. 2 shows the data obtained from Injection No. 2. Injection No. 2 shows that the middle peak II (hGH) is absent on the column 42 side showing removal of this component by the antibody. The shoulder on peak I is due to splitting of eluting peaks due to the size-exclusion properties of the protein G column used for column 42.

Figure 4:
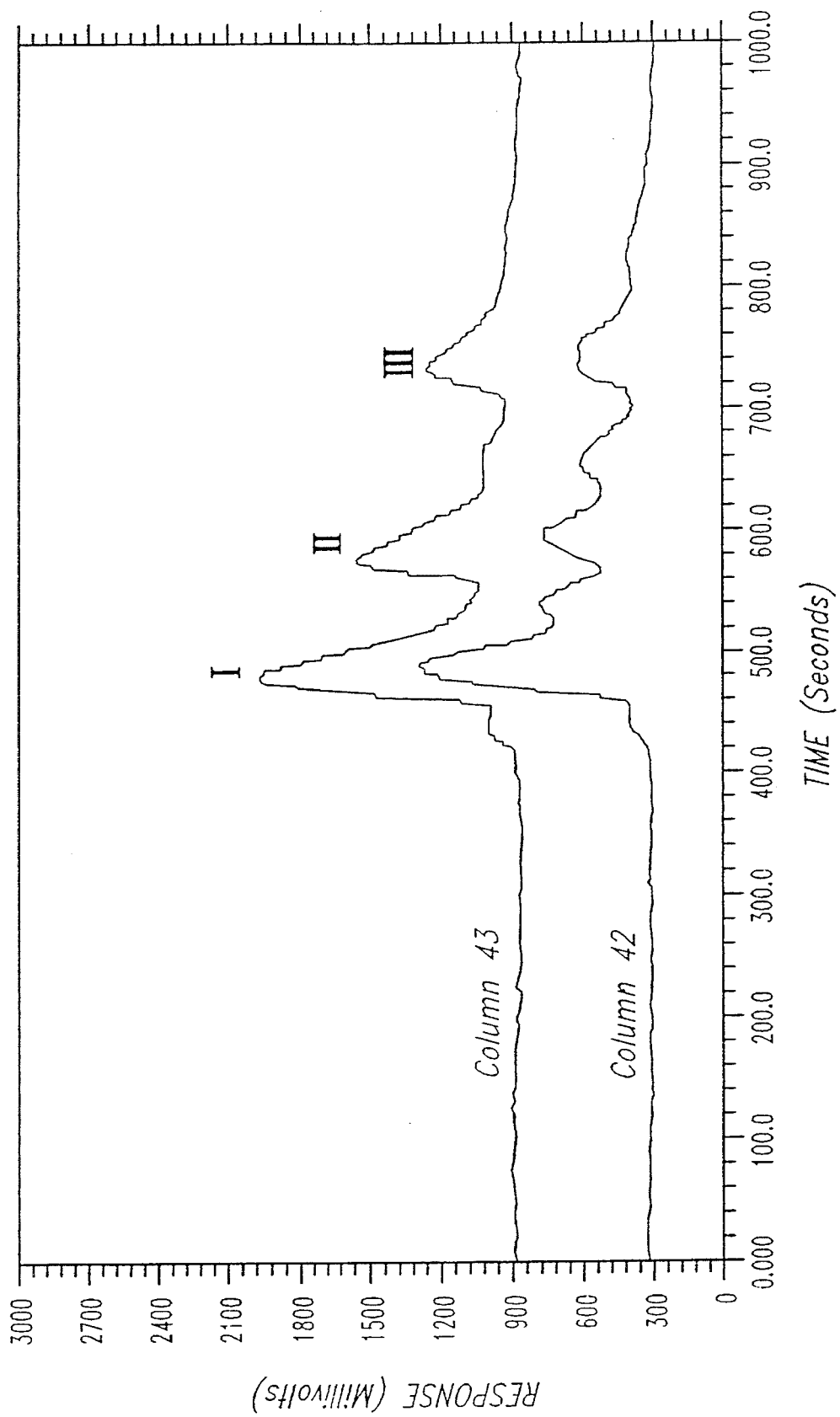
Figure 5:
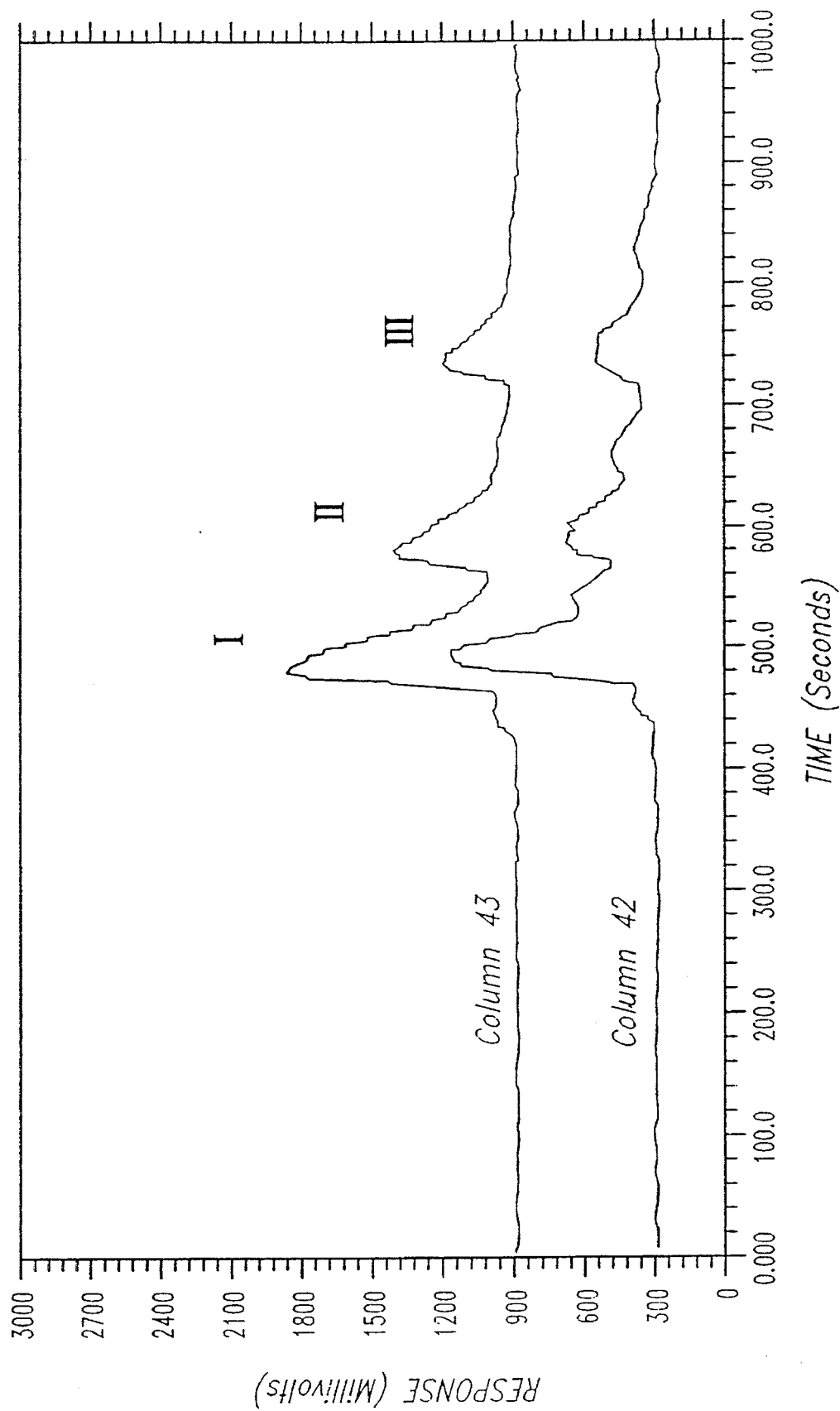

Injection No. 3 (see FIG. 4) is a 100 μl sample at 0.5 AUFS. Note the reappearance of peak II. The reappearance of peak II shows that GHC072 (the antibody) is saturated. This injection was repeated (Injection 4) and is shown in FIG. 5. Then columns 42 and 43 were eluted with 20% acetic acid until the absorbance reached a baseline. Then, the whole system was re-equilibrated in the tris/$Na_2SO_4$ mobile phase and left overnight.

Figure 6:
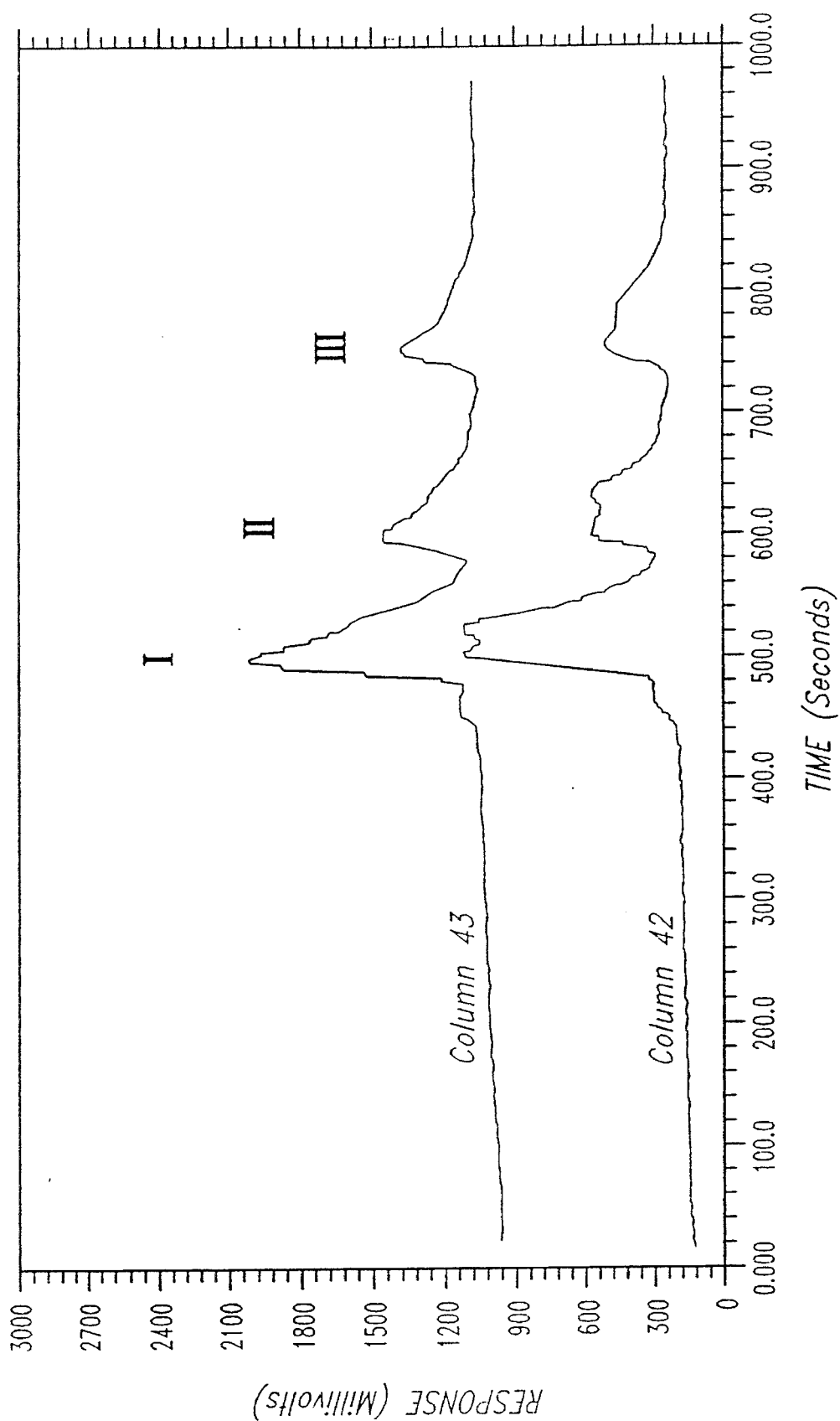

Injection 6 (FIG. 6) shows again that, except for minor splitting of peaks on the column 42 side, the detectors give equivalent responses to the sample. This is after antibody has been applied (i.e. during injections 1, 2, 3 and 4) and then eluted off with 20% acetic acid.

Figure 7:
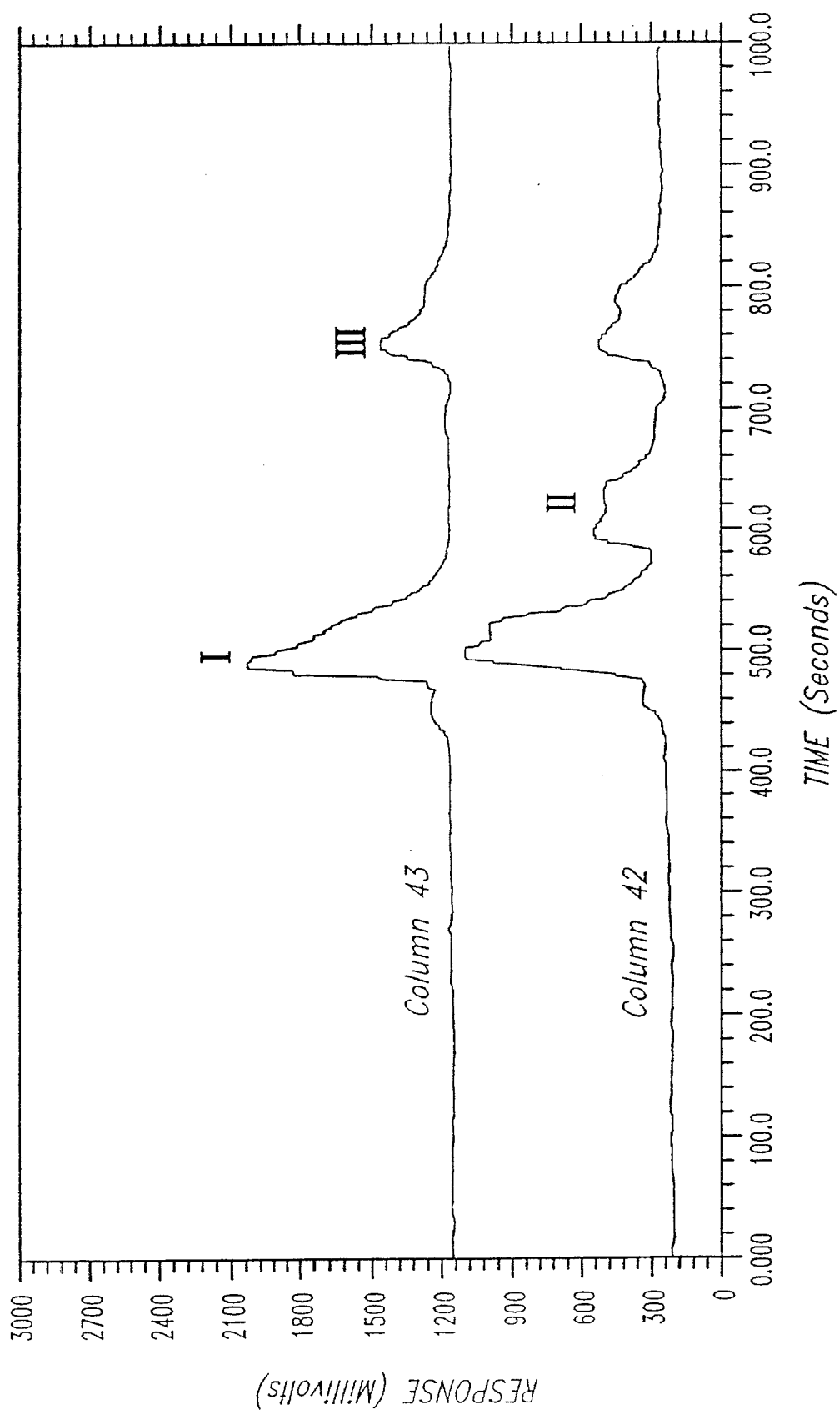
Figure 8:
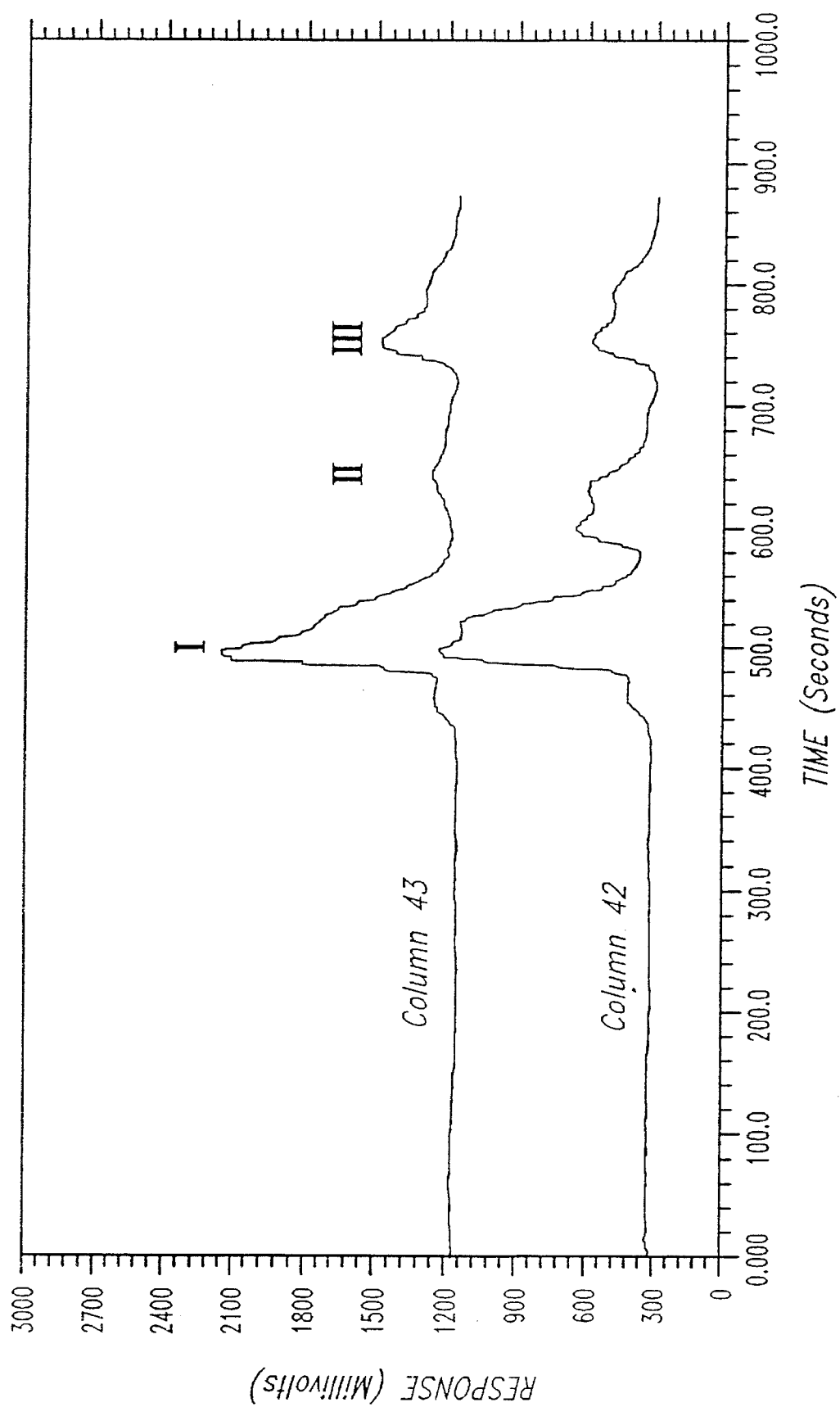
Figure 9:
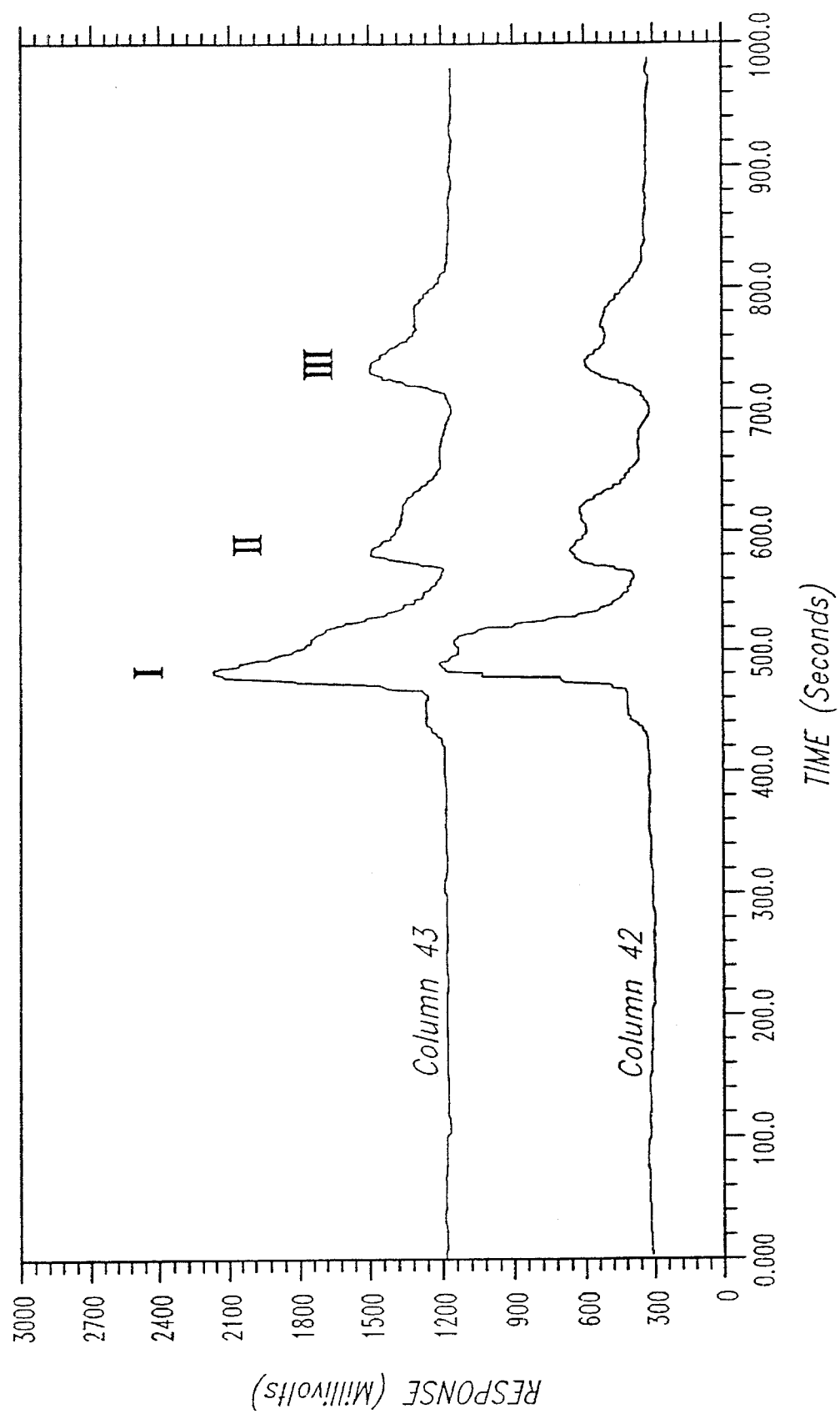

Next, column 43 was loaded with GHC072 as was done before with column 42 and the sample was injected again. As can be seen on injection 7 (FIG. 7), once again the hGH peak disappears, as expected, on the column 43 side. On injection 8 (FIG. 8), partial restoration of the hGH peak on the column 43 side is seen. On injection 9 (FIG. 9), the peak is restored entirely now that the antibody capacity is exceeded.

It is clear that better matched PRG columns (less size exclusion characteristics), a digital subtraction and inversion would produce a peak at position II and thus the operation of an antigen-selective detector has been demonstrated. The extension into other antibodies and their specific antigens is obvious as protein G will bind virtually any mammalian species' IgG.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for determining the presence of an antigen of interest in a sample comprising of:
    (a) segregating the sample into a plurality of distinct zones by chromatography;
    (b) splitting the segregated sample into a first stream and a second stream;
    (c) contacting the first stream with a first solid phase having immobilized thereon capture ligands that specifically bind the antigen of interest;
    (d) contacting the second stream with a second solid phase substantially identical to the first solid phase except lacking the immobilized capture ligands; and
    (e) determining whether said first solid phase and said second solid phase differentially bind the antigen of interest, wherein differential binding of antigen determines the presence of the antigen of interest.

2. The method of claim 1 which includes performing the segregation step by high performance liquid chromatography.

3. The method of claim 1 wherein said capture ligands are antibodies.

4. The method of claim 1 wherein said capture ligand is selected from the group consisting of a lectin, recombinant protein A, and recombinant protein G.

5. The method of claim i wherein said determining includes assaying the first and second streams after said contacting steps by a technique selected from the group consisting of ultraviolet light adsorption, fluorescence, refractive index, radioactivity, electrochemical activity, and any combination thereof.

6. The method of claim 1 wherein the first and second solid phases are each packed in a column.

7. A device for determining the presence of an antigen of interest in a sample eluted through a chromatographic column in a flow of eluant, comprising:

(a) means for splitting the flow of eluant from a chromatographic column into at least a first stream and a second stream;

(b) a capture component including a first solid phase having immobilized thereon capture ligands that specifically bind to the antigen of interest, said capture component coupled to said splitting means to accept a first stream of eluant flow from the splitting means;

(c) a control component including a second solid phase substantially identical to the first solid phase except lacking the immobilized capture ligands, said control component coupled to said splitting means to accept a second stream of eluant flow from the splitting means; and (d) one or more detectors effective to determine differential binding of the suspected antigen by said capture component and said control component, said detectors coupled to said capture component to accept therefrom the stream of eluant exiting said capture component and coupled to said control component to accept therefrom the stream of eluant exiting said control component.

8. The device of claim 7 wherein said capture ligands are antibodies.

9. The device of claim 7 wherein said capture ligands are selected from the group consisting of a lectin, recombinant protein A, and recombinant protein G.

10. The device of claim 7 wherein said detectors assay the first and second streams by a technique selected from the group consisting of ultraviolet light adsorption, fluorescence, refractive index, radioactivity, electrochemical activity, and any combination thereof.

11. The device of claim 7 wherein the first and second solid phases are each packed in a column.

12. A device for determining the presence of an antigen of interest in a sample in a flow of eluant comprising:

(a) a chromatographic column;

(b) means for splitting the flow of eluant from said chromatographic column into at least a first stream and a second stream;

(c) a capture component including a first solid phase having immobilized thereon capture ligands that specifically bind the antigen of interest, said capture component coupled to said splitting means to accept a first stream of eluant flow from the splitting means;

(d) a control component including a second solid phase substantially identical to the first solid phase except lacking the immobilized capture ligands, said control component coupled to said splitting means to accept a second stream of eluant flow from the splitting means; and (e) one or more detectors effective to determine differential binding of the suspected antigen by said capture component and said control component, said detectors coupled to said capture component to accept therefrom the stream of eluant exiting said capture component and coupled to said control component to accept therefrom the stream of eluant exiting said control component.

* * * * *

UNITED STATES PATENT AND TRADEMARK OFFICE
CERTIFICATE OF CORRECTION

PATENT NO.    :   5,491,096

DATED         :   February 13, 1996

INVENTOR(S)   :   J. Richard Sportsman

It is certified that an error appears in the above-identified patent and that said Letters Patent is hereby corrected as shown below:

In the claims, column 6, line 57, delete "i" and insert --1-- therefor.

Signed and Sealed this

Eighteenth Day of June, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,491,096
DATED : February 13, 1996
INVENTOR(S) : J. Richard Sportsman It is certified that error appears in the above-indentified patent and that said Letters Patent is hereby corrected as shown below:

In column 4, line 53, change "skated" to --stated--.

In column 5, line 1, please replace "claim i" with -- claim 1 --.

Signed and Sealed this

Twelfth Day of November, 1996

Attest:

BRUCE LEHMAN

Attesting Officer    Commissioner of Patents and Trademarks